United States Patent
Kania

[11] Patent Number: 5,603,122
[45] Date of Patent: Feb. 18, 1997

[54] FORM-FIT SOCK

[76] Inventor: Bruce Kania, 717 S. Fourteenth St., Bozeman, Mont. 59715

[21] Appl. No.: 406,145
[22] Filed: Mar. 20, 1995
[51] Int. Cl.$^6$ .................................................. A61F 2/78
[52] U.S. Cl. ........................................ 2/239; 2/22; 623/36
[58] Field of Search ............................. 623/36, 33, 32, 623/34, 35, 37; 2/239, 16, 241, 22; 602/62, 63

[56] References Cited

U.S. PATENT DOCUMENTS

| | | |
|---|---|---|
| 1,319,637 | 11/1919 | Blevens . |
| 1,497,219 | 6/1924 | Martino . |
| 2,002,064 | 5/1935 | Kohl . |
| 2,666,208 | 1/1954 | Funk .................................... 2/239 |
| 2,703,405 | 3/1955 | Smallberg, Sr. ...................... 2/239 |
| 3,451,232 | 6/1969 | Belzidsky . |
| 3,457,566 | 7/1969 | Artzt ..................................... 2/239 |
| 3,520,002 | 7/1970 | Wellington . |
| 3,600,717 | 8/1971 | McKeehan ........................... 623/36 |
| 3,855,677 | 12/1974 | Belizidsky ......................... 28/72 R |
| 4,369,284 | 1/1983 | Chen . |
| 4,502,234 | 3/1985 | Schaefer et al. ..................... 36/28 |
| 4,618,213 | 11/1986 | Chen . |
| 4,635,626 | 1/1987 | Lerman ............................. 128/365 |
| 4,840,635 | 6/1989 | Smith et al. ......................... 623/36 |
| 4,908,037 | 3/1990 | Ross .................................... 623/32 |
| 4,923,474 | 4/1990 | Klasson et al. ...................... 623/33 |
| 5,007,937 | 4/1991 | Fishman et al. ..................... 623/34 |
| 5,108,456 | 4/1992 | Coonan, III ......................... 623/37 |
| 5,211,667 | 5/1993 | Danforth ............................. 623/35 |
| 5,258,036 | 11/1993 | Edenbaum et al. ................. 623/33 |
| 5,258,037 | 11/1993 | Caspers ............................... 623/36 |
| 5,262,468 | 11/1993 | Chen . |
| 5,263,923 | 11/1993 | Fujimoto ............................. 602/62 |
| 5,314,496 | 5/1994 | Harris et al. ........................ 623/31 |
| 5,314,497 | 6/1994 | Fay et al. ............................ 623/34 |
| 5,443,525 | 8/1995 | Laghi .................................. 623/25 |

FOREIGN PATENT DOCUMENTS

1812982A3  4/1993  U.S.S.R. .

OTHER PUBLICATIONS

Brochure—TEC Interface Systems.
Brochure—Silosheath.
Brochure—Alps Clearsheath.
Brochure—Ipos, Ipocon.
Technical Bulletin—Shell Chemical Company, "Kraton Thermoplastic Rubgers in Oil Gels".

*Primary Examiner*—Amy B. Vanatta
*Attorney, Agent, or Firm*—Oblon, Spivak, McClelland, Maier & Neustadt, P.C.

[57] ABSTRACT

A form fitting sleeve member for an amputee's residiuum which eliminates air pocket formation and skin irritation. The sleeve member has a bias pattern and a contoured form fit. The sleeve may have polymeric cushioning material arranged on its interior surface to provide an interface between an amputee's residuum and a prosthetic device.

19 Claims, 4 Drawing Sheets

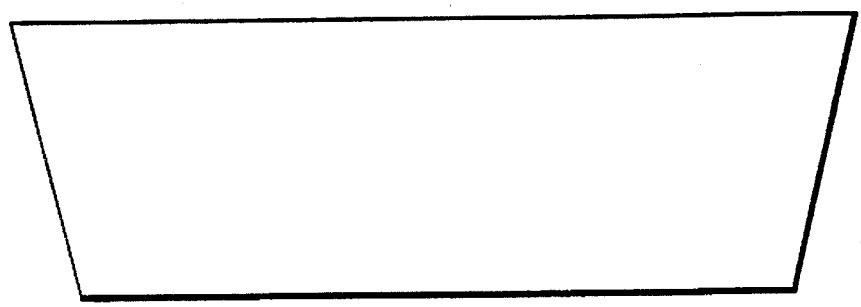
FIG. 3A
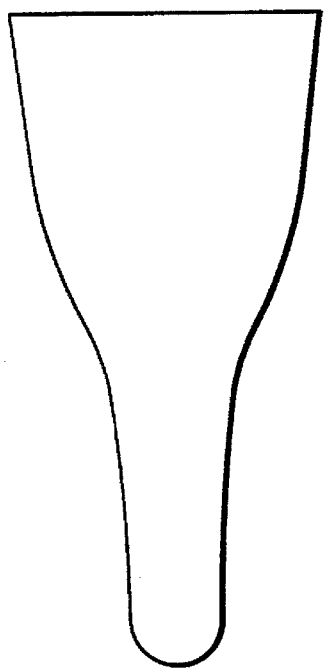 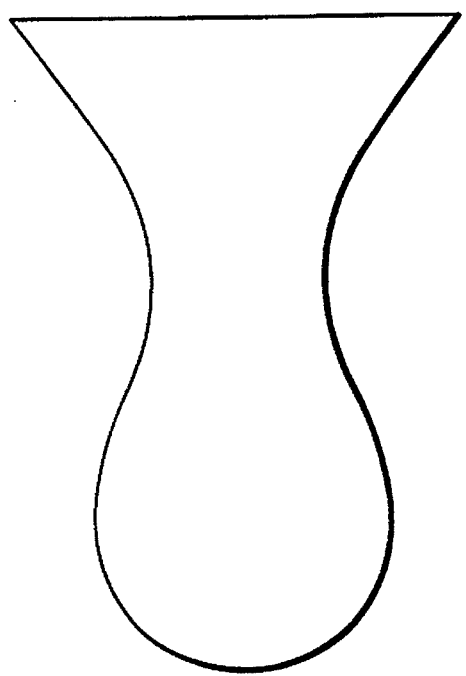
FIG. 3B    FIG. 3C

FORM-FIT SOCK

BACKGROUND OF THE INVENTION

1. Field of the Invention

The present invention relates to a sleeve member for enclosing an amputation stump, preferably to a cushioned sock for use by, e.g., below-knee (BK) amputees. The sleeve member is provided in a contoured form fit configuration which adapts to a right or left side bias of the bony prominence of the residuum (stump). Cushioning material may optionally be provided on the inside and/or outside of the sleeve to minimize the discomfort of a prosthetic device, such as an artificial arm or leg. In a preferred embodiment, the cushioning material is in a recessed achilles configuration: the cushioning material does not contact the wearer at an upper posterior ( i.e., knee crease), or upper anterior (i.e. elbow crease, etc.) portion of the residuum.

2. Discussion of the Background

For at least the past 80 years amputees have worn tubular socks over their residual limb. Cotton, wool and cotton-wool blends have typically been used. More recently, with the advent of synthetic materials, nylon and other textiles, including some with a measure of elasticity, have also been utilized.

In a typical below-knee (BK) prosthesis an amputee's stump tends to "piston" in the socket: during ambulation the stump will come up in the socket of the prosthesis until the attaching means holding the prosthesis to the wearer cause the prosthesis to lift with the stump. On the way down, air may be trapped between the residuum and stump sock, or between the prosthesis socket and sock, or between a socket liner and a sock.

With wool and cotton socks which tend to breathe and which are not airtight this pistoning effect is not a major problem with regard to the generation of sound effects. Since wool and cotton tend not to tightly form fit a residuum, however, the amputee typically packs a material around the residuum once it is placed into the prosthetic device or adds additional socks to increase thickness or puts on thicker socks in order to provide necessary fit. However, for socks which do not breathe and which are made from, e.g., polymeric material, a problem occurs when the residuum pistons in the prosthetic device: terrific sound effects such as sucking and gurgling noises are generated which are obtrusive and inappropriate, often embarrassing the wearer. In addition, such air pockets produce non-uniform pressures and loading discontinuities on the skin, irritating it.

Finally, many amputees experience a swelling of the stump. When the residuum is in a prosthetic socket the stump tends to contract significantly, and when taken out of the socket the stump tends to expand within minutes of removal. This expansion and contraction of the residuum contributes to the development of air pockets and the generation of obtrusive noises since a sock which may have provided a comfortable fit on the expanded stump becomes a loose fit with air pocket opportunities when the residuum is placed inside the prosthetic socket. In addition, and over time, an amputee's residuum tends to adjust in size, usually shrinking. As these changes occur they increase the tendency for the pistoning effect, described above, to occur. In addition to the embarrassment caused by the sound effects generated by pistoning, cushioned socks which allow or promote air pocket formation quickly wear out and, if not replaced often, lead to lesions, etc. on the residuum.

Currently available cushioned residuum socks are tubular or conical and do not provide a form fit on an amputee's residuum. Regardless whether such socks are provided with internal and/or external cushioning material they fail to avoid air pockets. While a stump may generally have a roughly conical or cubical shape there are invariably recessed areas on, e.g., the medial side of the prominent tibia bone. Generally, on a below knee, left side residual limb the recessed area will be predominantly on the right side of the tibia bone. There is also typically a smaller recessed area on the left side. For right side residual limbs the predominant recessed area is on the left side of the bone, with smaller recessed areas on the right side. Usually the greatest recess occurs immediately below the patella, on either side. In addition, left side amputees typically have a right side bias to the bony prominence of the below knee stump, and right side amputees have a similar bias to the left side. Conventional tubular or conical elastic socks simply cannot account for these several variable conditions without using extremely high levels of elastic tension which compress the outer-most points along the stump's circumference, causing discomfort and a non-uniform fit.

SUMMARY OF THE INVENTION

Accordingly, one object of this invention is to provide a novel optionally cushioned sleeve member for enclosing an amputation stump having a form-fitting tubular shape.

Another object of the present invention is to provide an optionally cushioned sleeve member having a bias pattern and contoured form fit which will equally accommodate a left side amputee and a right side amputee.

Another object of the present invention is to provide a cushioned sock having a contoured form fit shape and polymeric cushioning material arranged to provide an interface between an amputee's residuum and a prosthetic device.

Another object of the present invention is to provide a non-cushioned sleeve member having a contoured form fit.

Another object of the present invention is to provide a cushioned sleeve member for enclosing an amputation stump having a contoured, form-fitting tubular shape wherein the interior of the closed end of the sleeve member is impregnated with a polymeric material arranged in a recessed achilles configuration which provides a cushioning effect at the interface between the residuum and a prosthetic device socket but which does not come into contact with the skin in the crease of the knee or elbow.

Another object of the present invention is to provide a cushioned sock which allows for the timed-release of a skin conditioner, biocide, etc.

Another object of the present invention is to provide a cushioned sleeve for an amputation residuum which is form fitting and which avoids the generation of air pockets and the obtrusive noises they provide.

Another object of the present invention is to provide a sleeve member for enclosing an amputation stump which is form fitting and which is optionally cushioned, which is as thin as possible.

Another object of the present invention is to provide a sock, including typical prior art tube socks, etc., having cushioning material on the inside thereof in a recessed achilles configuration.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 shows a typical banded asymmetric pattern for the three-piece form fitting sleeve member according to the invention, piece a being optional on the FIG. 3 pattern asymmetric pattern. Piece a band can also be used in the FIG. 1 pattern to provide a top band banded reflected pattern.

DETAILED DESCRIPTION OF THE PREFERRED EMBODIMENTS

The present invention sleeve member for enclosing an amputation stump overcomes the problems encountered with prior art tubular or conical socks which are either prone to air pocket sound effects or are so constricted as to be uncomfortable by providing a sleeve member which is made from a pattern and from a textile material which provides elastic tension such that the sleeve member form fits an amputee's residuum. This combination of sleeve pattern and textile material provide a sleeve member having a comfortable feel and avoiding the generation of obtrusive sounds which are directly traceable to the presence of air pockets between a sleeve member and an amputee's residuum. The sleeve of the invention has enough elastic compression to form fit a stump but is not so tight as to be considered a stump shrinker, as in U.S. Pat. No. 4,840,635 incorporated herein by reference.

Figure 1B:
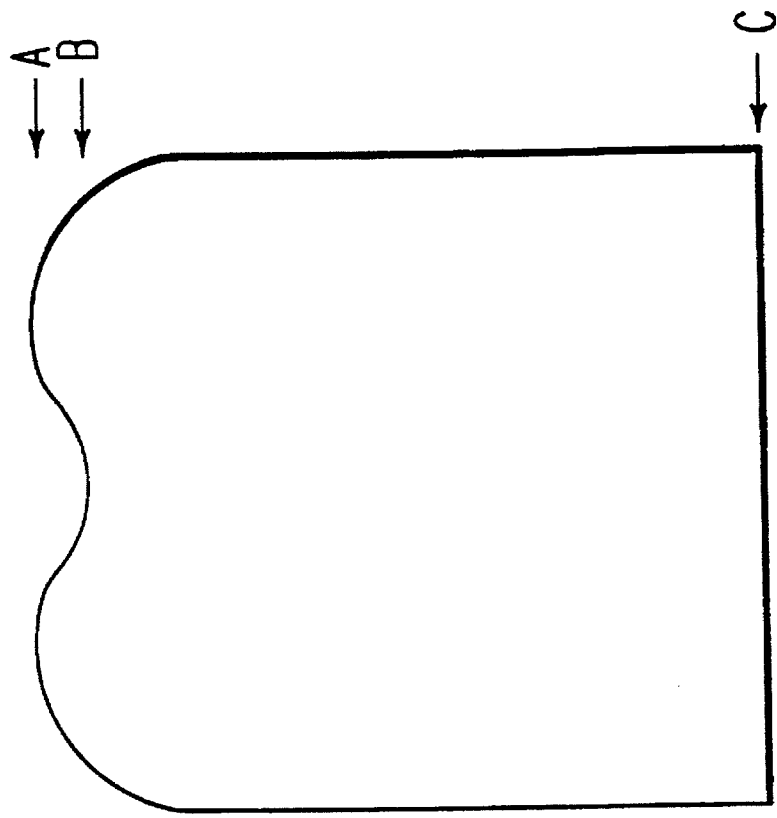
FIG. 1 shows a typical reflected pattern for the two-piece form fitting sleeve member according to the invention. Pattern member a is a bell-shaped piece, pattern member b is a bactrian-shaped piece.
Figure 1A:
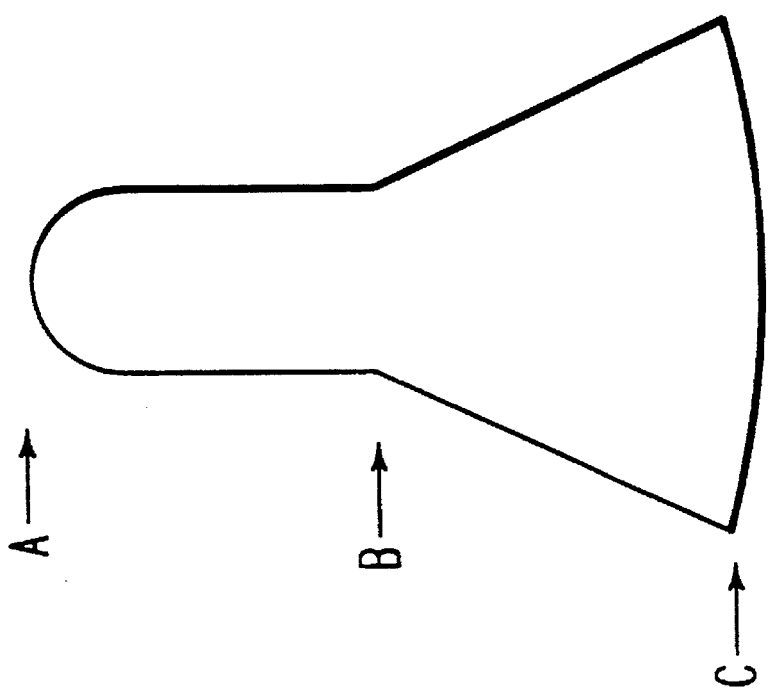
Figure 2B:
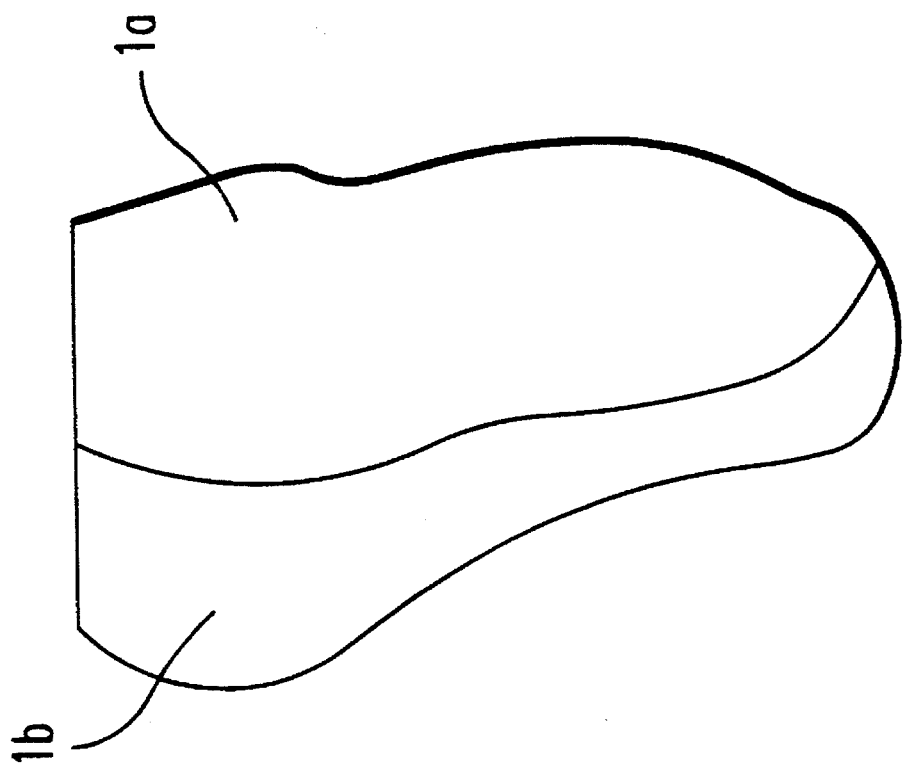
FIG. 2 shows frontal (A) and side views (B) of the invention sleeve member enclosing a stump-like form, where 1a and 1b refer to pattern members a and b, respectively, in FIG. 1.
Figure 2A:
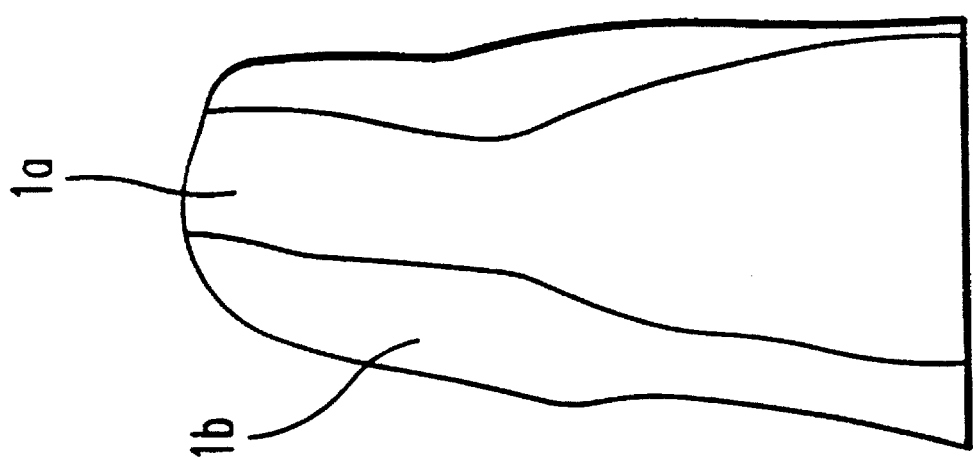
Figure 4:
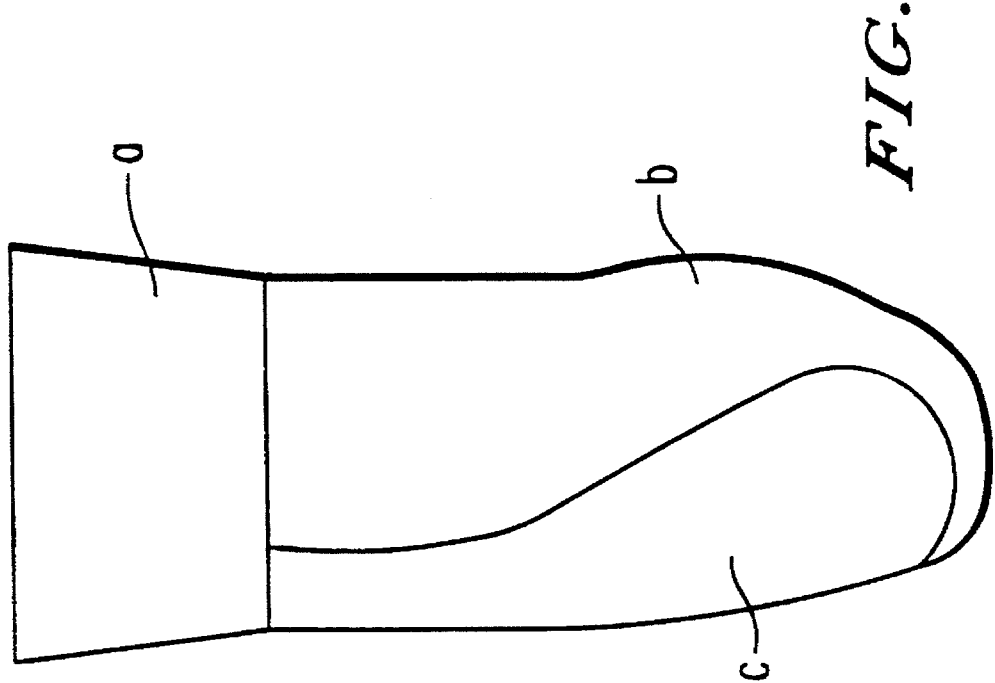
FIG. 4 shows an invention sleeve member assembled from the FIG. 3 pattern, where a (trapezoidal, b (penduloid) and c (paraboloid) correspond to patterns a, b and c, respectively, in FIG. 3.

FIG. 1 depicts a typical pattern from which the present invention form-fitting sleeve member is constructed. The pattern is a reflected two-piece pattern, one piece of which is designed to cover the bony prominence of a typical BK stump, (FIG. 1a) the other piece joined to the first at the edges thereof and circumscribing the typical onset of soft tissue around the stump (FIG. 1b). The two patterns are used to cut out two or more pieces of textile material which are brought together such that the "X" on each of the patterns in FIGS. 1a and 1b are in contact with the "X" on the other pattern, followed by the sewing together of the edges of each pattern in typical fashion. When the two pieces are sewed together, a sleeve member is provided which has a form fitting tubular shape having an open end into which an amputation stump may be introduced, a closed end opposite to the open end, an interior and an exterior. The two-piece pattern may be cut out of the same textile material or different textile materials, and the two pieces of textile material may have the same color or different colors. The three-piece pattern of FIG. 3 banded asymmetric also provides a form-fit sleeve, piece a being optional asymmetric.

The form fit sleeve of the invention is made from fabric according to the patterns in FIG. 1 or FIG. 3. In FIG. 1a the distance A-B divided by the distance B-C generally varies from $2/1$ to $1/2$ and is preferably about $1/1$. The width of the pattern in FIG. 1a at point B divided by the width at point C is generally approximately from $1/4$–$1/1$, preferably about $1/2$. In FIG. 1b the distance A-C divided by the distance B-C is generally preferably about 1.05–1.3, most preferably about 1.1. In both patterns of FIGS. 1 and 3 the dimensions may be varied so as to provide a comfortable form fit that avoids air pockets.

The two or more pieces of textile material used to form the invention form fitting sleeve member can be sewn together using any type of thread and any type stitch. In a preferred embodiment, woolly nylon is used to interconnect the two-piece form-fitting sleeve member of the invention using a flatlocked stitch, which is a stitch well known to those in the art. This flat-locked stitch tends to create a smooth, non-irritating seam having a stretch comparable to jersey fabric.

The size of the sleeve member according to the invention can be varied depending upon the residuum to be enclosed by simply proportionally reducing or enlarging the pattern, as desired. The term "form fitting tubular shape" as used herein refers to the shape of the invention sleeve member which provides a contoured fit on an amputation stump, which substantially reduces or eliminates air pockets during pistoning of the amputation stump in a prosthetic socket and which is obtained by providing a sleeve member composed of two or more pieces of fabric having the pattern described in FIG. 1 or FIG. 3.

The sleeve member according to the present invention may be made of any textile material having any thickness (ply). Preferred textile fabrics are those having elasticity, such as stretchable non-wovens (e.g., the Xymid® line of fabrics including Wearforce® fabrics from DuPont which connect bulkable yarns with non-woven sheet substrates), Lycra® comprising segmented elastomeric polyurethane fibers (spandex), supplex nylon (an engineered nylon textile fabric with a cotton-like texture and appearance), neoprene fabrics (polychloroprene fabrics), nylon, spunbonded olefin, looped nylon, spunlaced fabrics, polyester, aramid fiber fabrics, etc. However, any textile material may be used such as those described in *Textiles,* fourth edition, N. Hollen et al, MacMillan, New York, 1973, *The Modern Textile Dictionary,* Duell, Sloan and Pearce, New York, 1963 and *Dyeing Chemical Technology of Textile Fibers,* Trotman, E., Charles Griffin and Co., London, 1975, all incorporated herein by reference. The fabrics used to make the invention sleeve member are preferably elastic and are preferably jersey knit but include all woven, knitted and non-woven textile fabrics. In addition to those mentioned above and described in the above-mentioned references, those described in Volume 22, p. 762 ff and Vol. 16, p. 72 ff of the Kirk-Othmer *Encyclopedia of Chemical Technology,* Wiley, New York, 1983 and 1981, respectively, are also included, both of these references being incorporated herein by reference.

Preferred fabrics include mixtures of the above-mentioned fabrics, such as a fabric of neoprene, 88% supplex nylon/12% lycra spandex, 85% nylon/15% lycra spandex, 94% polyester/6% lycra spandex. Such mixed fabrics may be uniformly mixed or may have one type of fiber or predominantly one type of fiber on one face thereof. For example, in those fabrics described above which contain lycra, the lycra can be mixed throughout, can make up the entire or substantially the entire face, or the entire or substantially the entire back of the fabric once it is arranged in an invention sleeve.

The textile fabrics used in the invention sleeve member may be treated/finished in any manner known in the art. For example, a nylon tricot surface may be applied to the textile fabric, etc. The finishing need not be uniform over the entire invention sleeve member. The sleeve member may be selectively treated at, for example, above the knee (or elbow) portions, and with the same treatment, no treatment or another treatment being present below the knee or elbow. Similarly, treatment on the outer surface of the invention sleeve member may be different from that on the inside thereof.

The textile material used to make the invention sleeve is preferably elastic (stretchable) in one or more, preferably two, directions and is capable of adjusting to variations in form and size of the residuum. In a preferred embodiment, a nylon, neoprene, looped nylon sleeve member combination provides excellent comfort and durability. Preferred thicknesses of the invention textile material range from 0.010 in–0.200 in, preferably 0.025 in to 0.125 in, all values and all ranges therebetween. Typically the thicknesses of patterns pieces in FIGS. 1 and 3 are the same, but need not be.

The sleeve member according to the invention is preferably a cushioned sleeve member, that is a sleeve member having a form fitting tubular shape with an open end into which an amputation stump may be introduced, a closed end opposite to said open end, an interior and an exterior, wherein the interior at the closed end is impregnated with a polymeric material arranged so as to provide a cushion between the amputee's residuum and any prosthetic device to be worn, attached to, etc. the residuum. The cushioning material is preferably a polymeric material, most preferably a thermoplastic elastomer such as a thermoplastic rubber, silicon containing elastomer, etc. which provides an interface between the residuum and a prosthetic device and which includes a recessed area towards the open end of the sleeve member, the recess overlying the back of the knee or elbow when worn by an amputee, such that the polymeric material does not contact the skin at the back of the knee or elbow when worn by an amputee. This cushionng material may also be a thermoset silicone. This cushioning material is thus provided in a "recessed achilles" arrangement which avoids the irritation occurring in the crease behind a knee or elbow provided by prior art cushion sleeves.

The polymeric material which provides the cushioning effect may be any polymeric material. Preferred materials are those elastomers described at pgs. 446–640 of Volume 8 of the Kirk-Othmer *Encyclopedia of Chemical Technology,* Wiley, New York, 1979 and those rubbers described in *Synthetic Rubbers: Their Chemistry and Technology,* Blackley, D., Applied Science Publishers, London, 1983 and *Rubber Technology,* Morton, M. Ed., Van Nostrand Reinhold Co., New York, 1987, all three references incorporated herein by reference. A preferred embodiment of the present invention sleeve member, when cushioned, includes a cushioning material of Kraton®-type rubber material including those obtained from Shell, CPT, and GLS. These Kraton® rubbers are styrene-ethylene/butylene-styrene block copolymers or styrene-ethylene/propylene block copolymers and are available in triblock or diblock form. See, e.g. the *Kraton® Technical Bulletin* from Shell Chemical Company, SC:1102-89, June, 1992, incorporated herein by reference.

The cushioning polymeric material used in the present invention cushioned sleeve member is characterized by a certain durometer range. Preferred durometers for the invention cushioning material range from 1–20 on the Shore "A" scale. The lower the number the softer the rubber, typically due to a higher level of plasticizer. A preferred durometer range is 3–14 including all values therebetween and all ranges therebetween.

The invention polymeric cushioning material may be a blend of, e.g., Kraton® rubbers and oils such as mineral oil, etc. including typical stabilizers, etc. which provide an average durometer of from 1–20, preferably 3–14. These blends typically comprise a rubber having a lower durometer (1–10 on the Shore "A" scale) and a rubber having a higher durometer (e.g., 11–20). The blends are preferably capable of being stretched 100% or more, preferably 400% or more before tearing and are capable of providing a form fit to the residuum due to their inherent elasticity. In addition, the low durometer Kraton® rubbers tend to have a sticky feeling which, when present in the polymeric cushioning material, tends to enhance the form fitability of the sleeve.

If desired, the present invention cushioning material may comprise antioxidants such as Vitamins A, B and C or any other antioxidants commonly used in polymers. In addition, skin conditioning agents may be added to the polymeric material of the present invention cushioned sleeve member to soothe the skin of the residuum during wear. Such skin conditioners include mineral oil, baby oil, etc. which may be added to the polymeric material prior to its application to the sleeve member. Also, astringents, biocides, medicaments, etc. may be added or applied to the cushioning material to avoid infection or heal sores, etc.

As described above, the cushioning material of the present invention cushioned sleeve member is preferably formed in a recessed achilles fashion on the interior of the sleeve member. Cushioning material may also be applied to the exterior of the sleeve member. In both cases, it is preferred that the cushioning material be applied such that it provides an interface between the amputee's stump and a prosthetic device but does not contact the skin at the back of the knee or elbow when worn by an amputee. The cushioning material may be separated from the skin by a piece of fabric, by an interior sock linen, or may contact the skin directly. Such contact with the skin can reduce sweating, etc. While several methods may be used to apply the cushioning material to the sleeve member to accomplish this result, a preferred method includes the dipping of the closed end of the tubular sleeve member into molten or liquified cushioning material at an angle of from 15° to 80°, preferably 20°–50°, most preferably 24°–45°, with respect to the surface of the molten or liquid cushioning material. In this manner, the cushioning material extends up the sleeve member from the closed end thereof to a further extent on the side of the sleeve member positioned in front of the knee than behind the knee (the pattern in FIG. 1a faces forward on a BK amputee). As long as the cushioning polymeric material does not contact the skin at the back of the knee or elbow when worn by an amputee but still provides an interface between the amputee's stump and a prosthetic device, the material is in a recessed achilles configuration. Preferably the polymeric material comes up at least about ½–10, preferably 3–8 inches, all values and ranges therebetween from the closed end of the sleeve in front of the knee or elbow and covers the knee. The difference in height of the cushioning material behind (i.e., in the crease of) the knee or elbow as opposed to in front of the knee or elbow can differ by several inches measured from the closed end of the sleeve member, typically from 1–8 inches, all values therebetween and all ranges therebetween. In a preferred embodiment the cushioning material is thicker at the closed end of the sleeve than it is towards the open end.

In addition to the application of the invention polymeric cushioning material to the sleeve member by dipping into liquified or molten polymeric material, it is possible to dissolve the polymeric material in a solvent followed by application of the solvent to the sleeve member with subsequent evaporation of the solvent. Close control of the thickness of the polymeric material is obtained using this method. In both the direct dipping and solvent methods the sock is generally spun to provide good coverage while drying. In general, the thickness of the polymeric material applied to the invention sleeve member in a recessed achilles fashion can be any thickness but preferably varies from 0.001–0.150 inches, all values and all ranges therebetween, and can be substantially nonconstant in thickness throughout. For example, the cushioning material preferably may be thicker at the closed end of the sleeve (e.g., 0.125 in thick) and be tapered or feathered in decreasing thickness as the open end is approached.

Another preferred method of producing the invention cushioned sleeve is injection molding. The sleeve is pulled over a core and inserted into a cavity with polymeric material being injected into the closed bottom end.

Other features of the invention will become apparent in the course of the following descriptions of exemplary embodiments which are given for illustration of the invention only and are not intended to be limiting thereof.

EXAMPLES

Example 1

A form-fit next-to-skin sock was prepared from an 88% supplex nylon/12% lycra spandex jersey knit fabric using woolly nylon thread and a serged flat-locked stitch. The sock comprises two pieces of fabric, the first piece having the pattern described in FIG. 1a, the second piece having the pattern described in FIG. 1b.

A mixture of melted Kraton® rubbers obtained from Shell (G1652) and GLS (6705) and Duoprime® 70 oil (mineral oil) was prepared, the sewn inverted sock was then placed over a mold facsimle of an amputation stump having recessed portions at what would be either side of the tibia and dipped into the molten Kraton® blend at an angle of 24°–28° with regard to the plane of the surface of the molten Kraton® and removed. The mold was spun during drying. A form-fit cushioned stump sock was obtained having adhered cushioning material in a recessed achilles arrangement on the interior thereof.

Example 2

A 1/16 inch thick neoprene textile fabric with nylon tricot surface treatment for above the knee contact was used to prepare a three-piece form fitting sleeve member according to the present invention using the pattern described in FIG. 3. The 1/16 inch neoprene material for the below the knee segment of the invention sleeve had nylon on the exterior side and looped nylon on the interior side. The against the skin side of the above knee segment of the invention sleeve was neoprene which provided a high friction bond. This form fitting sock was dipped into molten Kraton® (a blend of tough and soft Kraton® used in Example 1) at an angle of 24°–28° to provide a cushion material on the interior thereof. The resultant composite sock of nylon, neoprene, looped nylon and cushioning rubber provides a durable cushioned sleeve member which, when impregnated with rubber, has an approximate thickness of 1/8 inch.

Example 3

A polartec 2000 stretch laminate fabric having an 85% nylon/15% Lycra® spandex face and a 94% polyester/6% Lycra® spandex back was used to prepare an invention sleeve member using the pattern described in FIG. 1. The resultant sleeve member is a form-fitting tubular member for enclosing an amputation stump.

Example 4

A commercial cotton tube sock is inverted and dipped into molten elastomer at an angle of 26° relative to the plane of the molten elastomer. A sock having cushioning material in a recessed achilles configuration is obtained.

What is claimed as new and desired to be secured by Letters Patent of the United States is:

1. A sleeve member for enclosing an amputation stump, said member having a form fitting tubular shape with an open end into which an amputation stump may be introduced, a closed end opposite said open end, an interior and an exterior, wherein said interior of said sleeve member is impregnated with a polymeric material arranged in a configuration such that said polymeric material provides an interface between said stump and a prosthetic device and includes a recessed area towards the open end of the sleeve member, said recess overlying the back of the knee or elbow when worn by an amputee, such that the polymer material does not contact the skin at the back of a knee or elbow when worn by an amputee, and wherein said polymer material has a thickness which is greatest at the closed end of the sleeve member.

2. The sleeve member as claimed in claim 1, wherein said polymeric material is a thermoplastic elastomer.

3. The sleeve member as claimed in claim 2, wherein said thermoplastic elastomer has a Shore A durometer of from 1–20.

4. The sleeve member as claimed in claim 1, wherein said polymeric material is a thermoplastic rubber.

5. The sleeve member as claimed in claim 1, wherein said polymeric material is a thermoset silicone resin.

6. A method for covering a stump, comprising donning the sleeve member of claim 1 over said stump.

7. A sleeve member for enclosing an amputation stump, said sleeve member having a form fitting tubular shape with an open end into which an amputation stump is introduced, a closed end opposite said open end, an interior and an exterior, said member being constructed of sewn-together pieces of textile fabric, said pieces of textile fabric being sewn together at edges thereof and having the shape of a reflected pattern consisting of bell-shaped and bactrian-shaped pieces or of an asymmetric pattern consisting of paraboloid-shaped, penduloid-shaped and, optionally, trapezoidal-shaped pieces.

8. The sleeve member as claimed in claim 7, wherein said textile fabric has the shape of a reflected pattern.

9. The sleeve member as claimed in claim 7, wherein said textile fabric has the shape of an asymmetric pattern.

10. The sleeve member as claimed in claim 7, wherein at least a portion of the interior thereof is coated with polymeric material such that said polymeric material provides an interface between said stump and a prosthetic device.

11. The sleeve member as claimed in claim 10, wherein said polymeric material is a thermoplastic elastomer.

12. The sleeve member as claimed in claim 11, wherein said thermoplastic elastomer has a Shore A durometer of from 1–20.

13. The sleeve member as claimed in claim 10, wherein said polymeric material is a thermoplastic rubber.

14. The sleeve member as claimed in claim 8, wherein said reflected pattern includes a circumferential band at the open end.

15. The sleeve member as claimed in claim 9, wherein said asymmetric pattern includes a trapezoidal-shaped piece.

16. A method for covering a stump, comprising donning the sleeve member of claim 7 over said stump.

17. A prosthetic device comprising the sleeve member of claim 15.

18. The device of claim 17, wherein said device is an artificial leg.

19. The device of claim 17, wherein said device is an artificial arm.

* * * * *